US012674205B2

(12) United States Patent
Olek et al.

(10) Patent No.: US 12,674,205 B2
(45) Date of Patent: Jul. 7, 2026

(54) CBX6 AS EPIGENETIC MARKER FOR THE IDENTIFICATION OF IMMUNE CELLS, IN PARTICULAR MEMORY B CELLS

(71) Applicant: PRECISION FOR MEDICINE GMBH, Berlin (DE)

(72) Inventors: Sven Olek, Berlin (DE); Udo Baron, Berlin (DE); Kati Bourquain, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 802 days.

(21) Appl. No.: 17/914,689

(22) PCT Filed: Mar. 25, 2021

(86) PCT No.: PCT/EP2021/057784
§ 371 (c)(1),
(2) Date: Sep. 26, 2022

(87) PCT Pub. No.: WO2021/191369
PCT Pub. Date: Sep. 30, 2021

(65) Prior Publication Data
US 2023/0151422 A1 May 18, 2023

(30) Foreign Application Priority Data
Mar. 27, 2020 (DE) ..................... 10 2020 108 560.5

(51) Int. Cl.
*C12Q 1/68* (2018.01)
*C07H 21/04* (2006.01)
*C12Q 1/6881* (2018.01)

(52) U.S. Cl.
CPC ..... *C12Q 1/6881* (2013.01); *C12Q 2600/154* (2013.01)

(58) Field of Classification Search
None
See application file for complete search history.

(56) References Cited

FOREIGN PATENT DOCUMENTS

WO 01/77384 A2 10/2001
WO 2012/162660 A2 11/2012
(Continued)

OTHER PUBLICATIONS

Kulis et al. (Nat Genetics, vol. 47, No. 7, pp. 746-756, Jul. 2015). (Year: 2015).*
(Continued)

*Primary Examiner* — Jeanine A Goldberg
(74) *Attorney, Agent, or Firm* — BakerHostetler

(57) ABSTRACT

The present invention relates to a method, in particular an in vitro method, for identifying memory B cells, comprising analyzing epigenetic modifications/properties of (including the methylation status) of at least one CpG position in the mammalian gene region for Chromobox protein homolog 6 (CBX6), wherein a demethylation or lack of methylation of said gene region is indicative for a memory B cell, when compared to a non-memory B cell. The analyses according to the invention can identify memory B cells on an epigenetic level and distinguish them from all other cells in complex samples, such as, for example, other blood or immune cells. The resent invention furthermore provides an improved method for quantifying memory B cells, in particular in complex samples. The method can be performed without a step of purifying and/or enriching cells, preferably in whole blood and/or non-trypsinized tissue.

Figure 1:
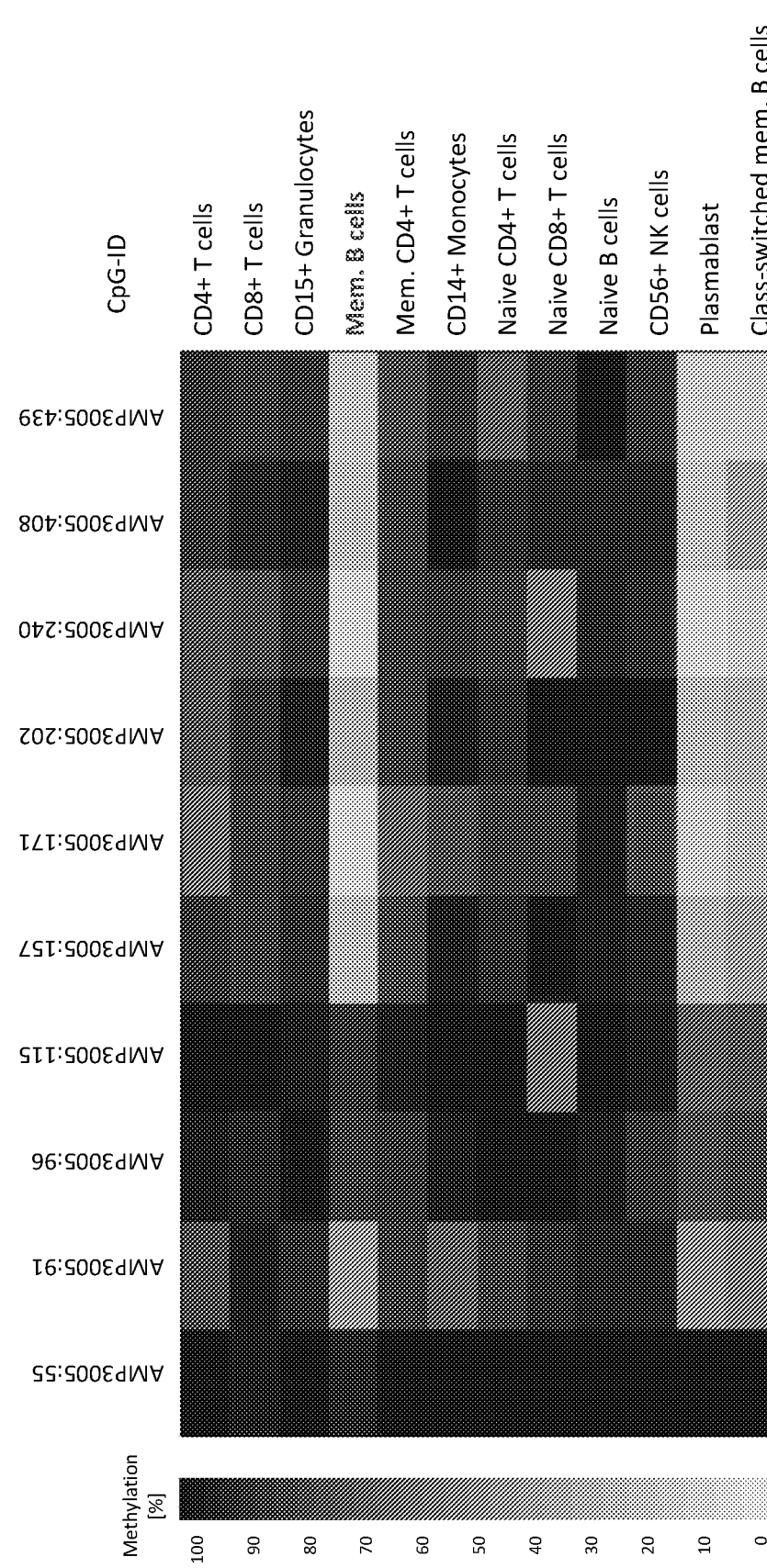

15 Claims, 6 Drawing Sheets
Specification includes a Sequence Listing.

(56)                    References Cited

FOREIGN PATENT DOCUMENTS

WO          2014170497 A2      10/2014
WO          2017/050916 A1      3/2017

OTHER PUBLICATIONS

Samans et al. (Frontiers in immunology, âEpigenetic immune monitoring for COVID-19 disease course prognosisâ, Mar. 14, 2023) (Year: 2023).*

Sanz, et al., "Phenotypic and functional heterogeneity of human memory B cells", Seminars in Immunology, vol. 20, No. 1, pp. 67-82, Feb. 2008.

Booth, et al., "Quantitative sequencing of 5-methylcytosine and 5-hydroxymethylcytosine at single-base resolution", Science, vol. 336(6083), pp. 934-937, 2012.

Antequera, et al., "Number of CpG islands and genes in human and mouse", Proceedings of the National Academy of Sciences, vol. 90(24), pp. 11995-11999, 1993.

Jones, et al., "Cancer-epigenetics comes of age", Nature Genetics, vol. 21(2), pp. 163-167, 1999.

Esteller, "CpG island hypermethylation and tumor suppressor genes: a booming present, a brighter future", Oncogene, vol. 21(35), pp. 5427-5440, 2002.

Laird, "The power and the promise of DNA methylation markers", Nature Reviews Cancer, vol. 3(4), pp. 253-266, 2003.

Zhang, et al., "Epigenetic regulation of B cell fate and function during an immune response", Immunological Reviews, vol. 288(1), pp. 75-84, 2019.

Coradini, et al., "Differential expression of genes involved in the epigenetic regulation of cell identity in normal human mammary cell commitment and differentiation", Chinese Journal of Cancer, vol. 33(10), pp. 501-510, 2014.

Kristensen, et al,. "PCR-based methods for detecting single-locus DNA methylation biomarkers in cancer diagnostics, prognostics, and response to treatment", Clinical Chemistry, vol. 55(8), pp. 1471-1483, 2009.

Lai, et al., "DNA methylation profiling in human B cells reveals immune regulatory elements and epigenetic plasticity at Alu elements during B-cell activation", Genome Res., vol. 23, No. 12, pp. 2030-2041, 2013.

Almen, et al., "Genome wide analysis reveals association of a FTO gene variant with epigenetic changes", Genomics, vol. 99, No. 3, pp. 132-137, 2012.

Database Accession No. ABF47028 "Oligonucleotide Seq Id No. 147025 for detecting SNP TSC0037103", p. 1, 2001.

Database Accession No. ABF77492 "Oligonucleotide Seq Id No. 177489 for detecting SNP TSC0044012", p. 1, 2001.

* cited by examiner

FIG. 2A SEQ ID NO: 1

FIG. 2B

GGAGGGAGGTCTCCCCCATAGGTGGCGGTGGTGGGACCAGATGGCCCAACAACTGGGAAAGAAGGGCAAGAAACCAAACTGCCCACTCACCAGCCCCTGGAGAAAATC
ACCAGTGACAACCCCACCCTCCCAAACCTCAGCTTGGGTTAGCTCCCGGGGACCTGCCGGGACTTGGTTGTCCTTTGAGCAAGCACGGGTGTGGAGATCTGGGT
CCAGGCCCCTCTCCACAGTGCCTGCGATGCCCAGCTGGGCCCAGCTGCCCAGCTGGGCCTGGCCCAGCCCCATCCTGACATTGCCAGCCTCCGCCCATCTGACATTGTTTTTTTTCTTAA
ATAGCTGCTTTCTCCCCGCCACCCCCGCCATAGGAATCCCACAATATTTTTTCTATTTCTTTTTGTTTTGTTTTTGCAAAACTAATTCTTTCACTTTCCT
GTCATAAAATCACCTCTGAAAACACACACTTCTTTACAAAAGTCACGAATGACACGAACTCTCAGCAAAACTCTGGAAACACACCTGTAACTGGCACCCAGTGGT
CACTCACCTGGGGAGGGGTCAGGGGAAATCACCTCCAAGGACAGGAGAAATACCAGCCCTTATTGGGCGAAAAGCCAATTGGCACTTGACGGCCCAAAAGCCAACACACAGG
GCCAGGGTAGGGAGGGGCCGAGGAGTATCAGCCCCCCGAGGGTCCCCGTTCCTGCGAGGTCCCCTGCCAAGCCTGCTTCTGATCGGCCTGCGCCTGTGGGCCCTGCTGGGCAGGGAGATTGG
GAAGGAAGGCAGCCTCCCATTCTTAGGACCAAAGGCGCACAATGGACACCCGGGAAGTGGCCCAGGCGGCCCAAGCTGGGCCTGGAGGAGGGCCAGCTCCAGCCA
CGCCTGGAACACGCCACCCTTTGCCTGCCTCCCGGGGCCTGCCCACTGGGCCTGGCCTAAGGCTGGGCTGTGGCCTGCGGGAAACAGAAGCTGCCC
TCTGGTCTCCCCTTTGCCTGCCTCCTTGCTTGTCTTCAGGCAGGCTGTGTGAGAAAGCCTCCGTGCTGTGAGAAAGAGGGGCTGGCTGTGAGAAGGGCTGGCTGGCTGGCAG
AGGACACGGGAGCCCTCCTTTGCTTGCTTCAGGGAGCTTGGAATGGGGTCTCCCTCTATCTCGGTCCCCTCTATCTCGGTGACTTCCAGAGCCTGGTCCCCAGGCGAGAGCCAGTC
CTCCCCAAACACCCGGAGGAAGAGAGGGAGCTTGGAATGGGGTCCCCTCTATCTCGGTCCCTCTATCTCGGTGACTTCCAGAGCCTGGTCCCAGGCGAGAGCCAGTC
GGGGGTGGGGGCACGGTGCCCCCAGGACACCTGGGCCACCTGGGCACCCGGGAGCCTGGCCTAGCACCCGGACCTTCCAGAGGTGCCCAGGCCTACTGAGCGGCCAGTC
CAGGCCTTCAATGCCCCTGTTCAAAGGAACTGTAAAGGGTCCTCGTAGCACCTTTGGTCAAGAAGGGCCTTTAGATGCGGGGGAGCTGAAGGGGTTTCCTCCCACCGTTGAGGGG
ACTGGAAGTTTCCACGGCAGGTTCTCGTAGCACCTTTGGTCAAGGAACTGAAGGGGTCCTTTAGATGCGGGGGAGCTGAAGGGGTTTCCTCCCACCGTTGAGGGG
GTTAGGAAAGAGCCAGGGCTGGGGCAGGGCTGGGCAGGGCATAGGGGTCTACTTAGGCCTCGTCAAACAGCAGGAAGCGCCCTCGTCTGCAGGCCTAGGGGCAGGGACTAGAGGGA
GGAGCCGAGTCAGGCCTCATCCTTGCCCAGGTTAGCACCGATGGCCAGGTTAGCACCATGCATCTGCCAGGAAGGGCCCTGTGTCACCCTCGGTGGG
GGCTCCTAAGGCCCTAGGCCCCCCACAGTGCCCAGGTTAGCACCGGCCCTGCCAGGTTAGCACCTAGCACCGAGAAATCAGACGCCCGAGAAGTGGGATGTGGAAGGGCAGAGAACCCTAGTTT
CTAGGGCTTTCCAGAAACCAGTGGCCCATTTGAGACAACAAGCAAAGCACAGCACCTGGGGTGGCTGGGGCAGGGGTGTGCCCTTTCTGGGGACCCCAACTACCCAGC
CCCATCCTCCTTGGTGAGCCCCCTCACTTGCTCGCCCAGTCGGTGACATCGTGACACCACATTGGAGCAGGGTGACATCTGCCCCCCCCCCCAAGCC
CCCCCTCCTTGGTGAGCCCCGCCCCCCAGCAGCTGTGGTGACATCGTGACATCTGCCCCCCCAATGCTGCCCCCCCAATGCTGCCCCCCAAGCC
TGACCGTCAGGAGGTTGCTGTGGTGACATCGTGACATCGTGACACCTGGACGAGGCAGCAGCCCCAGTCCCCGCCTCGGGAGGAGCACCGGCCTGCGGCCGGCCGTG
GGAGGTGCCGGGCCCGGCGCCCGCCAGCAGCTGTGGTGACCTGTGCTGCCTTGCTGGCTTGCCAGCTGCCCCGCTTCCGGCTTGCCACCGTGCCGGCCGATGG
GCTCACGGGTCTCGGGGAGGAGCTTGGGGGGCTGAGGGCTGAGCCTCAGCCTTGCGTGTCGTGCTGCTACCAGGGGGACCTGGGGCGGCGTAGGGGCGGGGGGCGG
CCAGAAGTAGCCCAGGGCCCGAGCCTGAGGGCTGAGCCTCAGCCTTGTACAGCGCAAAGGCGGCTTGTACAGCGCCAAAGGCGGCTTCATGTGCCGATCTGT
GTACGCCAGGACGCGCTCTCGCTGAACTTCTTGCTCTTGCTCCTATAACGCGGTTCCCGAGGGGACTTTCCGCGGGGCACTTTCCGCGGGCCCCAGCGCCCTT
GTCGATCACCTTCAGGTTCAGGGATGATGCCGGGTTCCCGCGCTTCACCTTGCGGTTGATGATGCCGCGTCCCGAGAAGGGCGAAATGGGGCGGCGAAATGGGGCGGGGGGC
TGCCCCCCTCGGGGTCCGGGGACGGGGGACATACGGTTGCAGCCGCGATGTCCTTCTTGCGGCGGACATGTCCTTGGGGCGGGCACTG
GCGCTCGGCTTGACAGAGAAATGCACATCACTGATGCCGAGGGCCTCGGCCTGGACCTTAAGATAATCACTGGTTCTTCAGGACTGGCTTGGCTGGCTTGGGACAGGGTTGGGTGGACCTGCCCCTGG
ATGTCCCTACGCCCCTAAGTAGAGCCTTCAGGTCAAGGTCAGGACCCTCGGCCTGGATCCCAGCTGGTCTTCAGGACTGGCTTAGAAAAGGAAACAGAGGTTCAGAGATG
AAGCAATTTGCCTGGACGCTCTCAAGTCAGGACACAGTGTCTGACAATTCCAAAACTGTGTTTTTCTATCACCACCTCTGTTAGCTCCACCACCTCTGTTAGCTCGGGGGCAGCCCTGGGCC
ACTCCATGGCTGCCCCTTGCTGACGCACAGGACAATTGGGACACCCCTGCCTAAACCCCTGCTAAACCCCTGCTCTGTGTGCAGATCCAGCCCA

```
CCAGATTGCA ACTTCTGCTT GGTAATTAGG CAAATGGAAA GCAGCAAGGG TGGACGGAGGG GCCCATGGAG GCTGATCTCC CAAGGGAGGC
CGATCCGTGC AAGTGTGTGG GAGGCGGGGG TACTAGAGAG GGGAGGAAGG AGGCTCCACT CACCCTCGGT CCCATCCACT CGGGCCCCCA
TGGGCACTGC CCACCTCAAG GCGGTGTGCC TGGTGCCTCT TCATGCACCA AGGCTGGCCC GGGCTGCTCC ACTTGGAGCT CAGGCCAGCA
GAAGCAGACC ACCTGTGGCA AGGGAAATGC ATTCCCTCTC CCCAGCCACC CCCAGGGGCC CAGCTTCTTG CCTCCTGAAG CCTGCATCCC
CTTTCAGGCC AGGGAGGCTC AGAGAGGTTG TGGGCTTTAG GGTGACCCGT GGGGAGGGAG GTCTCCCCCA TAGGGTGGCG GTGGTGGGGA
CCAGATGGCC CAACAACTGG GAAAGGAACA GAAGGGGGCA AGAAACC
```

CBX6 AS EPIGENETIC MARKER FOR THE IDENTIFICATION OF IMMUNE CELLS, IN PARTICULAR MEMORY B CELLS

CROSS-REFERENCE TO RELATED APPLICATIONS

This application is the National Stage Application of International Patent Application No. PCT/EP2021/057784, filed on Mar. 25, 2021, which claims the benefit of German Patent Application No. DE 10 2020 108 560.5, filed on Mar. 27, 2020, which are hereby incorporated by reference in their entirety.

SEQUENCE LISTING

The instant application contains a Sequence Listing which is being submitted herewith electronically in ASCII format and is hereby incorporated by reference in its entirety. Said ASCII copy, created on Sep. 26, 2022, is named 113828_000029_Sequence_Listing.txt and is 21,957 bytes in size.

The present invention relates to a method, in particular an in vitro method, for identifying memory B cells, comprising analyzing epigenetic modifications/properties of (including the methylation status) of at least one CpG position in the mammalian gene region for Chromobox protein homolog 6 (CBX6), wherein a demethylation or lack of methylation of said gene region is indicative for a memory B cell, when compared to a non-memory B cell. The analyses according to the invention can identify memory B cells on an epigenetic level and distinguish them from all other cells in complex samples, such as, for example, other blood or immune cells. The present invention furthermore provides an improved method for quantifying memory B cells, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure memory B cells of the blood within any solid organs, tissue or body fluid of a mammal.

BACKGROUND OF THE INVENTION

B cells develop from hematopoietic precursor cells in an ordered maturation and selection process. Memory B cells are a B cell sub-type that are formed within germinal centers following primary infection and are important in generating an accelerated and more robust antibody-mediated immune response in the case of re-infection.

Ag-activated B cells may undergo differentiation into memory B cells or short and long-lived PCs. The differentiation into memory B cells may occur with or without T cell help and in a germinal center (GC)-dependent or independent manner. This results in memory B cells subsets that differ in their effector function and overall capacity for protection.

Sanz et al. (Sanz I, Wei C, Lee F E, Anolik J. Phenotypic and functional heterogeneity of human memory B cells. *Semin Immunol.* 2008; 20(1):67-82) describe that memory B cells are more heterogeneous than previously thought. Despite initial descriptions of CD27 as a universal marker of human memory cells, memory populations were described that lack expression of CD27 and may be substantial in SLE and in some infections such as RSV. Additional heterogeneity of memory B cells can also be demonstrated on the basis of the expression of CD38, CD21, CD24, CD19, B220, FcRH4 and CD25.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxylcytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

Zhang and Good-Jacobson (in: Epigenetic regulation of B cell fate and function during an immune response. Immunol Rev. 2019 March; 288(1):75-84) disclose that epigenetic modifications are crucial for ensuring that the appropriate genes are transcribed or repressed during B cell differentiation. Recent studies have illuminated the changes in DNA methylation and histone post-translational modifications that accompany the formation of germinal center and antibody-secreting cells during an immune response. In particular, the B cell subset-specific expression and function of DNA methyltransferases and histone-modifying complexes that mediate epigenome changes have begun to be unraveled.

In view of the above, it is an object of the present invention to provide an improved and in particular specific and robust method based on DNA-methylation analysis as a superior tool in order to more conveniently and reliably detect, identify, discriminate, and quantify memory B cells.

The present invention solves the above object by providing a method for identifying memory B cells in a sample, comprising analyzing the methylation status (bisulfite convertibility) of at least one CpG position in the mammalian (e.g. human) gene region for Chromobox protein homolog 6 (CBX6), wherein preferably said gene region as analyzed is positioned based on/according to SEQ ID No. 1, wherein further preferably said gene region as analyzed is positioned based on/according to SEQ ID No. 2, wherein a demethylation or lack of methylation of said gene region is indicative for a memory B cell, when compared to a non-memory B cell.

CBX6 (Chromobox 6 or Chromobox protein homolog 6) is a component of a Polycomb group (PcG) multiprotein PRC1-like complex, a complex class required to maintain the transcriptionally repressive state of many genes, including Hox genes, throughout development. PcG PRC1 complex acts via chromatin remodeling and modification of histones; it mediates monoubiquitination of histone H2A 'Lys-119', rendering chromatin heritably changed in its expressibility. The gene for human CBX6 is found on chromosome 22, NC_000022.11.

Coradini et al. (in: Differential expression of genes involved in the epigenetic regulation of cell identity in normal human mammary cell commitment and differentiation. Chin J Cancer. 2014; 33(10):501-510) disclose expression patterns of a panel of 369 genes known to be involved in the establishment and maintenance of epithelial cell identity and mammary gland remodeling in cell subpopulations isolated from normal human mammary tissue and selectively enriched in their content of bipotent progenitors, committed luminal progenitors, and differentiated myoepithelial or differentiated luminal cells. Differential expression of four genes involved in cell identity maintenance was found: CBX6 and PCGF2, encoding proteins belonging to the Polycomb group, and SMARCD3 and SMARCE1, encoding proteins belonging to the Trithorax group.

In the context of the present invention, the gene region shall comprise all of the genomic region relating to and encoding for CBX6. Thus, included are enhancer regions, promoter region(s), introns, exons, and non-coding regions (5'- and/or 3'-regions) that belong to CBX6. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the CBX6 gene by the inventors, as specific epigenetic marker, allowing the identification of memory B cells as well as the clinical routine application of said analysis.

In the context of the present invention, the genomic region of CBX6, in particular according to SEQ ID No. 1, more preferably SEQ ID NO. 2 (Amp 3005), allows for the identification of memory B cells. Surprisingly, the discriminatory pattern of bisulfite convertible and non-convertible cytosine is particularly and preferably exclusively limited to the genomic region according to SEQ ID No. 1 for memory B cells as shown using the amplicon according to SEQ ID No. 2.

The inventors could demonstrate that in the memory B cells the CpG motifs as disclosed are almost completely demethylated (i.e. to more than 70%, preferably 80%, preferably, more than 90% and most preferred more than 95%, even more than 98%), whereas the same motifs are nearly completely, and preferably completely methylated in non-memory B cells. This is referred to herein also as "demethylation" or "lack of methylation".

The differential methylation of the CpG motifs within the aforementioned regions is a valuable tool to identify memory B cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of memory B cells without purification or any staining procedures.

Another preferred aspect of the method according to the present invention then further comprises a quantification of the relative amount of memory B cells based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region of CBX6 (e.g. of SEQ ID No. 1) as described and analyzed herein. Most preferred is a quantification of the relative amount of memory B cells is based on an (preferably parallel or simultaneous) analysis of the relative amount of bisulfite convertible DNA of cell-specific region for CBX6, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID No. 1, preferably oligomers according to any of SEQ ID No. 3 to 10.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the CBX6 gene region is produced that is a particularly preferred "tool" for performing the method(s) according to the present invention. Consequently, oligomers according to any of SEQ ID No. 3 to 10 or an amplicon as amplified by a primer pair based on SEQ ID No. 3 and 4 or 5 and 6 or 8 and 9 as mentioned herein constitute preferred embodiments of the present invention. Thus, the sequences of SEQ ID No. 1 to 2 (and, if needed, the complementary sequences thereto) can be used to design primers for amplifications, i.e. serve as "beacons" in the sequence as relevant. Similarly, additional primers and probes can be designed based on the amplicon according to SEQ ID No. 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID No. 1, and is preferably selected from the CpG positions 55, 91, 96, 115, 157, 171, 202, 240, 408, and 439 in the amplicon 3005 according to SEQ ID No. 2, and is more preferably selected from CpG positions 91, 157, 171, 202, 240, 408, and 439 in a fragment of the amplicon 3005 according to SEQ ID No. 2. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 157, 171, 202, 240, 408, and 439 in the amplicon No. 3005 of the CBX6 specific bisulfite convertible region (SEQ ID No. 1), or all sites as present on the bisulfite convertible region according to SEQ ID No 1. One or more of positions 96, and/or 115 in AMP 3005 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said memory B cells from all major peripheral blood cell types and/or non-blood cells, preferably, but not limited to, CD4+ T cells, memory CD4+ T cells, CD8+ T cells, CD15+ granulocytes, CD14+ monocytes, naive CD4+

T cells, CD56+NK-cells, naive CD8+ T cells, naive B cells, and other cell types derived from other organs than blood, in particular from naive B cells.

In yet another preferred embodiment of the method according to the present invention, the sample is selected from a mammalian body fluid, including human blood samples, or a tissue, organ or a sample of lymphocytes or a purified or separated fraction of such tissue, organ or lymphocytes or a cell type sample. Preferably, said mammal is a mouse, goat, dog, pig, cat, cow rat, monkey or human. The samples can be suitably pooled, if required. Preferably said cells are human cells.

Another preferred aspect of the method according to the present invention then further comprises the step of concluding on the immune status of said mammal based on said memory B cells. The memory B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of memory B cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said memory B cells as e.g. a sample for cell transfer into a patient.

Another preferred aspect of the method according to the present invention then relates to a method as above, further comprising formulating said memory B cells as identified for transplantation into a patient. Pharmaceutical preparations for these purposes and methods for their production are performed according to methods known in the art of transplantation medicine.

Another preferred aspect of the method according to the present invention then further then relates to a method for treating a condition or disease in a mammal, in particular in a human, comprising a method according to the invention as above, and the step of transplanting memory B cells as identified (e.g. in an aliquod taken from the sample) and isolated/multiplied in cell culture into a patient. Pharmaceutical preparations for these purposes and methods for their production are performed according to methods known in the art of transplantation medicine. The transplant can be autologous or allogenic.

Another preferred aspect of the method according to the present invention then further then relates to a method for treating and/or preventing a condition or disease in a mammal, in particular in a human, comprising a method according to the invention as above including a suitable treatment for said condition or disease comprising providing chemical and/or biological substances as above, and adjusting said treatment of the underlying disease or condition based on the results as provided by the method(s) of the invention. This may comprise the step of concluding on the immune status of said mammal based on said memory B cells. The memory B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status. This basis allows for adjusting said treatment, if necessary. Such adjustments may comprise the step of transplanting memory B cells as identified and isolated/multiplied in cell culture into a patient as above, and/or providing additional chemical and/or biological substances for adjusting said treatment and/or prevention.

One particular example is a method for treating and/or preventing a condition or disease in a mammal, in particular in a human, wherein first a vaccine is provided to said mammal. Respective vaccines and vaccination strategies are known, generally, vaccines contain the same germs (sometimes inactivated) that cause disease, or immunogenic parts thereof, optionally with suitable carriers and adjuvants. The success of a vaccine is dependent on the generation and maintenance of immunological memory, and the immune system can remember previously encountered pathogens, and memory B cells are critical in secondary responses to infection. Therefore, the method then comprises measuring and/or monitoring the amount of memory B cells in response to said vaccination(s) that is/are provided to said mammal. In case of an insufficient number of memory B cells, said treatment (here: vaccination) is adjusted, i.e. preferably a booster shot is given. The method may be repeated until sufficient immune cells (i.e. a substantial population of memory B cells) can be detected.

Another particular example is a method for generating immunity against an antigen comprising the method as above comprising providing at least one antigen as a vaccine, and detecting a sufficient immunity based on the population of memory B cells as identified in response to said at least one antigen as provided as said vaccine.

Treatment and/or prevention shall herein relate to the curing, prevention or alleviation of a disorder or malfunction of the body, i.e. bringing a body back to its healthy state.

Pharmaceutical preparations for these purposes and methods for their production are performed according to methods known in the art of a treatment using chemical and/or biological substances or transplantation medicine. Again, the transplant can be autologous or allogenic.

Another preferred aspect of the method according to the present invention relates to an oligomer according to any of SEQ ID No. 3 to 10, or an amplicon according to SEQ ID No. 2.

Yet another preferred aspect of the present invention then relates to a kit for identifying, quantifying, and/or monitoring memory B cells in a mammal based on the analysis of the bisulfite accessibility of CpG positions in the gene region for CBX6, comprising components for performing a method according to invention as described herein, in particular a kit comprising a) a bisulfite reagent, and b) materials for the analysis of the methylation status of CpG positions selected from the CpG positions in the region according to SEQ ID NO: 1 or 2, such as an oligomer selected from the sequences according to SEQ ID No. 3 to 10, or an amplicon as amplified by a primer pair based on SEQ ID No. 3 and 4 or 5 and 6 or 8 or a primer pair based on SEQ ID No. 3 and 4 or 5 and 6 or 8, respectively.

The present invention also encompasses the use of oligomers or amplicon or a kit according to the present invention for identifying and/or for monitoring memory B cells in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxylcytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

$$\text{Biomarker Ratio}=a/b$$

$a=\Sigma(\text{C and/or mC and/or hmC and/or fC and/or cC})$
$b=\Sigma(\text{C and/or mC and/or hmC and/or fC and/or cC})$,
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxylcytosine (cC)) and (ii) non-bisulfite convertible cytosine ((including 5-methyl-cytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosy-lation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the CBX6 genetic region and in particular the amplicon as described herein as a marker, the inventors very specifically identified, quantified and particularly differentiated memory B cells, and in their relation to other cell types in a sample, for example to other blood cells.

The invention will now be further described in the following examples and with reference to the accompanying figures and the sequence listing, without being limited thereto. For the purposes of the present invention, all references as cited herein are incorporated by reference in their entireties.

FIG. 1 shows the analysis of CpG sites on amplicon No. 3005 (SEQ ID No. 2) according to the invention. The columns in the table correspond to the CpG positions in the amplicon as analyzed (e.g. CpG 1, 2, etc.) with the positions indicated (AMP3005: 55 corresponding to CpG at position 55 of Amplicon 3005 according to SEQ ID No. 2, . . . etc.), and the rows correspond to the cell types as analyzed.

Figure 2A:
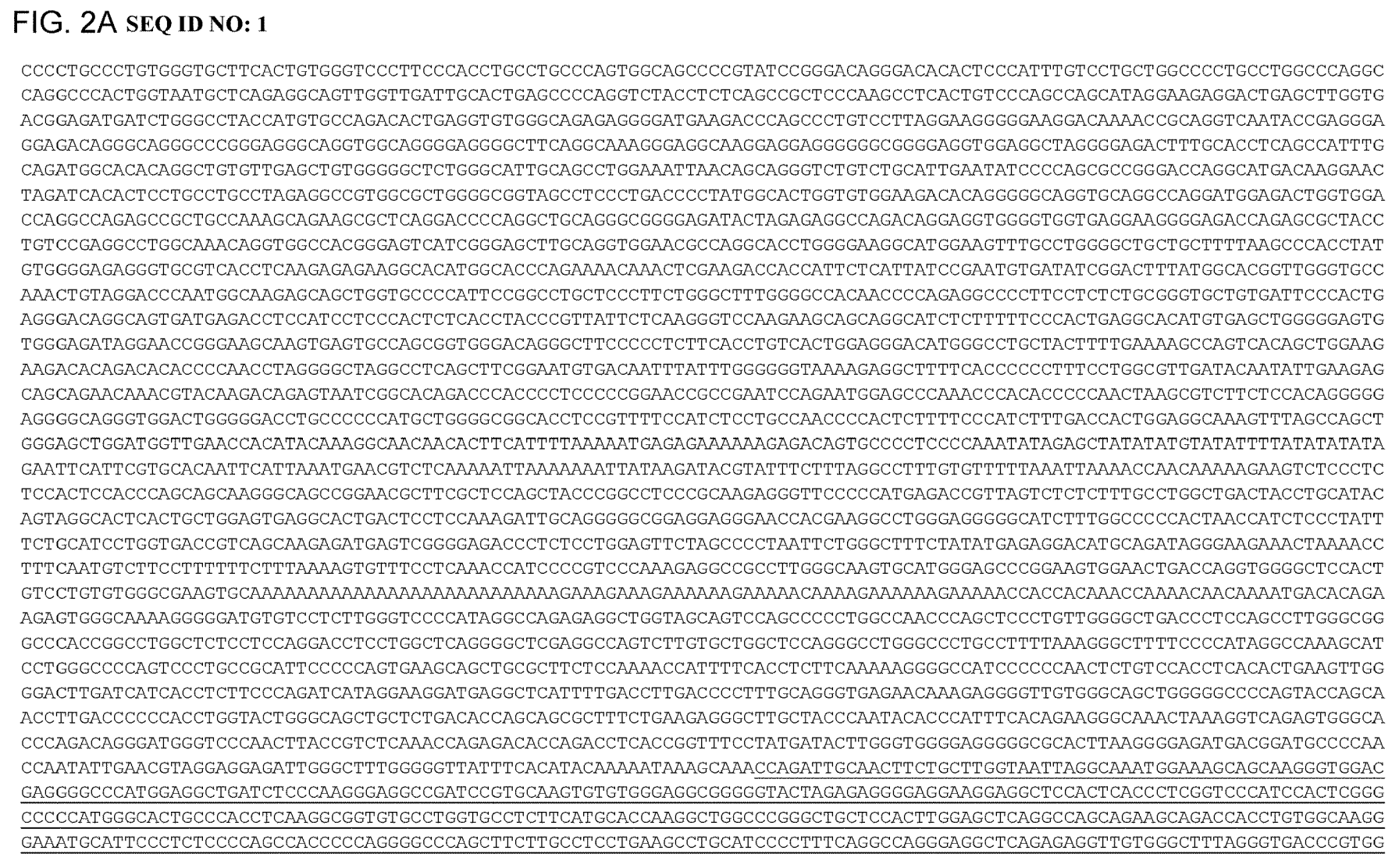
Figure 2C:
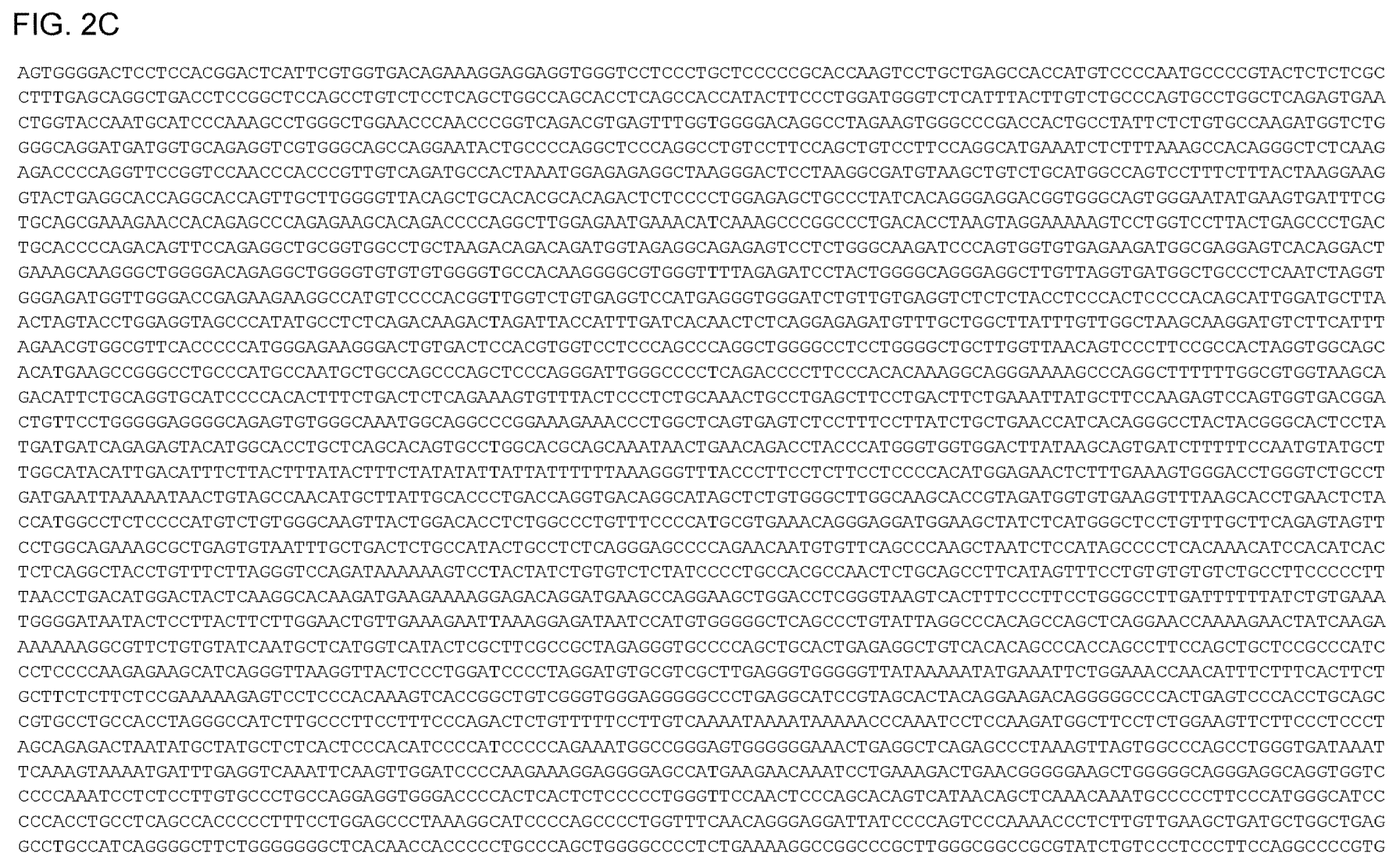
Figure 2D:
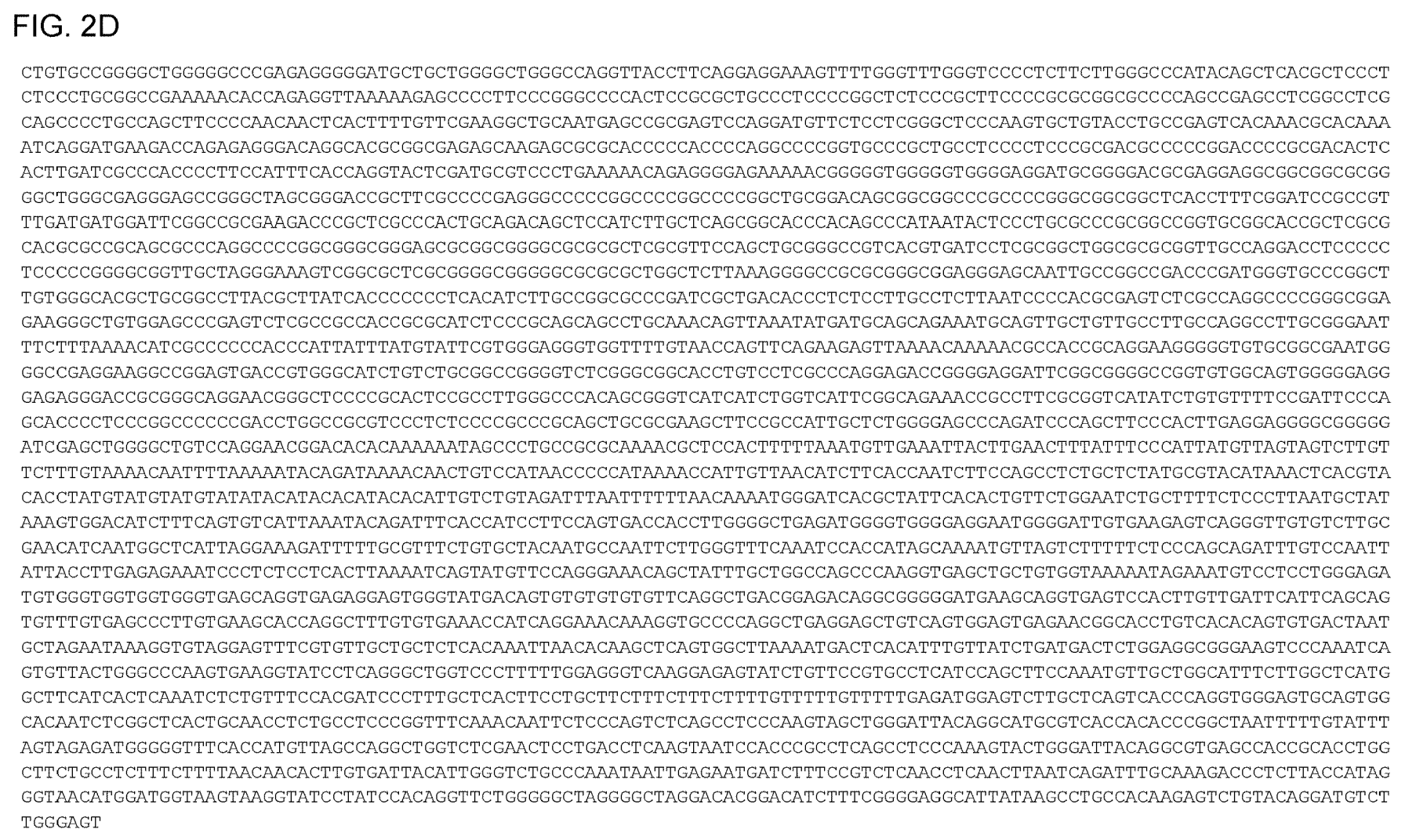

FIG. 2A, FIG. 2B, FIG. 2C, and FIG. 2D show the genomic region of the amplicon according to the present invention (SEQ ID No. 1, the amplicon sequence (SEQ ID NO. 2) is underlined.

FIG. 3 shows the genomic sequence of the amplicon according to the present invention (SEQ ID No. 2), the relevant CpG positions are bold and underlined.

SEQ ID No. 1 shows the sequence of the genomic region (genomic sequence with the Ensembl-coordinates 22:38860000:38875000:1) of the amplicon No. 3005 according to the present invention (see also FIG. 2A-FIG. 2D). *Homo sapiens* chromobox 6 (CBX6), transcript variant 1, mRNA, NCBI Reference Sequence: NM_014292.5.

SEQ ID No. 2 shows the genomic sequence of amplicon No. 3005.

SEQ ID Nos. 3 to 10 show the sequences of specific oligomers (primers and probes) according to the present invention.

EXAMPLES

Example 1

In order to identify memory B cells, qPCR was performed on bisulphite converted samples stemming from the human genomic region according to the sequence SEQ ID No. 1 (see FIG. 2A-FIG. 2D), in particular the region AMP3005 (underlined, and see FIG. 3).

For the actual epigenetic profiling of the amplicon region in blood cell subtypes, the immune cell populations as analyzed were as shown in FIG. 1.

The bisulfite-converted target-regions of preferred qPCR-assay-system as developed were:

Oligonucleotides for Bisulfite Sequencing (5'-3')

Forward Primer-
(SEQ ID NO: 3)
TTAGATTGTAATTTTTGTTTGGTAA

Reverse Primer-
(SEQ ID NO: 4)
AATTTCTTACCCCCTTCTATTC

Oligonucleotides of qPCR Assay (TpG Variant i.e., demethylation-specific; 5'-3')

Forward Primer-
(SEQ ID NO: 5)
GGAAAGTAGTAAGGGTGGAT

Reverse Primer-
(SEQ ID NO: 6)
CCCTCTCTAATACCCCCA

Probe-
(SEQ ID NO: 7)
TTGATTTGTGTAAGTGTGTGGGAGGTGG

Oligonucleotides of qPCR Assay (CpG Variant i.e., methylation-specific; 5'-3')

Forward Primer-
(SEQ ID NO: 8)
GGAAAGTAGTAAGGGTGGAC

Reverse Primer-
(SEQ ID NO: 9)
CCCTCTCTAATACCCCCG

Probe-
(SEQ ID NO: 10)
TCGATTCGTGTAAGTGTGTGGGAGGCGG

The cell type specificity (FACS-sorted immune cell preparations with memBLC qPCR) was found as follows (table 1):

| Cell type | Description | Demethylation (%) |
|---|---|---|
| Memory B cells | CD3–/CD20+/IgD–/CD27+ | ≥99.9 |
| Memory B cells | CD19+/IgD–/CD27+ | ≥99.9 |
| CD19+ B cells | CD19+ | 22.61 |
| Naïve B cells | CD3–/CD20+/IgD+/CD27– | 5.61 |
| Naïve B cells | CD19+/IgD+/CD27– | 1.99 |

-continued

| Cell type | Description | Demethylation (%) |
|---|---|---|
| Granulocytes | CD15++ | 0.23 |
| T Helper cells | CD3+CD4+ | 2.17 |
| T Helper cells | CD3+/CD8−/CD4+ | 2.53 |
| Cytotoxic T cells | CD3+/CD8+/CD4− | 1.65 |

-continued

| Cell type | Description | Demethylation (%) |
|---|---|---|
| Cytotoxic T cells | CD3+/CD8+/ | 1.22 |
| CD56+ NK cells | CD3−/CD56+/CD16+ | 0.17 |
| Monocytes | CD14+ | 0.20 |

The invention claimed is:

1. A method for producing an amplicon, the method comprising a) bisulfite treating isolated genomic DNA from a mammalian cell sample to generate bisulfite treated DNA, and b) producing the amplicon by amplifying from the bisulfite treated DNA of the mammalian gene region for chromobox protein homolog 6 (CBX6) comprising SEQ ID NO: 2, wherein at least one cytosine-phosphate-guanine (CpG) position in SEQ ID NO: 2 comprises bisulfite convertible cytosine, and wherein the amplicon comprises TG at the respective CpG position comprising the bisulfite convertible cytosine.

2. The method according to claim 1, wherein said at least one CpG position is selected from the CpG at positions 91, 157, 171, 202, 240, 408, and 439 in SEQ ID NO: 2, and wherein the amplicon comprises TG at least one CpG position.

3. The method of claim 1, wherein the bisulfite convertible cytosine is detected by a method selected from a methylation specific enzymatic digest, bisulfite sequencing, promoter methylation analysis, CpG island methylation analysis, MSP, and other methods relying on a detection of amplified DNA.

4. The method of claim 1, wherein said sample is selected from a mammalian body fluid, human blood samples, a tissue, organ, cell type blood sample, a sample of blood lymphocytes or a fraction thereof.

5. The method of claim 1, wherein said method is performed without a step of purifying and/or enriching said cell sample.

6. The method of claim 1, wherein said cell sample is from a mammal that suffers from or is likely to suffer from autoimmune diseases, transplant rejections, infection diseases, cancer, and/or allergy.

7. The method of claim 1, wherein the method is performed using a kit comprising a) a bisulfite reagent, and b) materials for detecting the bisulfite convertible cytosine.

8. The method according to claim 1, wherein said gene region comprises a bisulfite convertible cytosine at CpG positions 157, 171, 202, 240, 408, and 439 in SEQ ID NO: 2, and wherein the amplicon comprises TG at the respective CpG positions 157, 171, 202, 240, 408, and 439 in SEQ ID NO: 2.

9. The method according to claim 1, wherein the mammalian cell sample is whole blood and/or non-trypsinized tissue.

10. The method of claim 1, wherein amplifying is performed with a polymerase chain reaction (PCR).

11. The method of claim 10, wherein the PCR is quantitative PCR (qPCR).

12. The method of claim 10, wherein the PCR is performed with one or more oligomers selected from SEQ ID NOs: 3-10.

13. The method of claim 10, wherein the PCR is performed with one or more oligomers selected from SEQ ID NOs: 5-7.

14. The method of claim 10, wherein the PCR is performed using a probe comprising the nucleic acid sequence of SEQ ID NO: 7.

15. The method of claim 1, further comprising c) detecting the amplicon with a probe comprising the nucleic acid sequence of SEQ ID NO: 7.

* * * * *

SEQUENCE LISTING

<160> NUMBER OF SEQ ID NOS: 10

<210> SEQ ID NO 1
<211> LENGTH: 15001
<212> TYPE: DNA
<213> ORGANISM: Homo sapiens

<400> SEQUENCE: 1

```
cccctgccct gtgggtgctt cactgtgggt cccttccac ctgcctgccc agtggcagcc      60
ccgtatccgg gacagggaca cactcccatt tgtcctgctg gccctgcct ggcccaggcc     120 aggcccactg gtaatgctca gaggcagttg gttgattgca ctgagcccca ggtctacctc     180
tcagccgctc ccaagcctca ctgtcccagc cagcatagga agaggactga gcttggtgac     240
ggagatgatc tgggcctacc atgtgccaga cactgaggtg tgggcagaga ggggatgaag     300
acccagccct gtccttagga aggggaagg acaaaaccgc aggtcaatac cgagggagga     360
gacagggcag ggcccgggag ggcaggtggc aggggagggg cttcaggcaa agggaggcaa     420
ggaggagggg ggcggggagg tggaggctag gggagacttt gcacctcagc catttgcaga     480
tggcacacag gctgtgttga gctgtggggg ctctgggcat tgcagcctgg aaattaacag     540
cagggtctgt ctgcattgaa tatccccagc gccgggacca ggcatgacaa ggaactagat     600
cacactcctg cctgcctaga ggccgtggcg ctgggcggt agcctccctg accccctatgg     660 cactggtgtg gaagacacag ggggcaggtg caggccagga tggagactgg tggaccaggc     720
cagagccgct gccaaagcag aagcgctcag gaccccaggc tgcagggcgg ggagatacta     780
gagaggccag acaggaggtg gggtggtgag gaaggggaga ccagagcgct acctgtccga     840
ggcctggcaa acaggtggcc acgggagtca tcgggagctt gcaggtggaa cgccaggcac     900
ctggggaagg catggaagtt tgcctggggc tgctgctttt aagcccacct atgtggggag     960
agggtgcgtc acctcaagag agaaggcaca tggcacccag aaaacaaact cgaagaccac    1020
cattctcatt atccgaatgt gatatcggac tttatggcac ggttgggtgc caaactgtag    1080
gacccaatgg caagagcagc tggtgcccca ttccggcctg ctcccttctg ggctttgggg    1140
ccacaacccc agaggcccct tcctctctgc gggtgctgtg attcccactg agggacaggc    1200
agtgatgaga cctccatcct cccactctca cctacccgtt attctcaagg gtccaagaag    1260
cagcaggcat ctctttttcc cactgaggca catgtgagct gggggagtgt gggagatagg    1320
aaccgggaag caagtgagtg ccagcggtgg gacagggctt cccctcttc acctgtcact    1380 ggagggacat gggcctgcta cttttgaaaa gccagtcaca gctggaagaa gacacagaca    1440 cacccccaacc taggggctag gcctcagctt cggaatgtga caatttattt ggggggtaaa    1500
agaggctttt cacccccctt tcctggcgtt gatacaatat tgaagagcag cagaacaaac    1560
gtacaagaca gagtaatcgg cacagaccca ccctccccc ggaaccgccg aatccagaat    1620
ggagcccaaa cccacacccc caactaagcg tcttctccac aggggaggg gcagggtgga    1680 ctgggggacc tgcccccat gctggggcgg cacctccgtt ttccatctcc tgccaacccc    1740
```

-continued

```
actcttttcc catctttgac cactggaggc aaagtttagc cagctgggag ctggatggtt   1800
gaaccacata caaaggcaac aacacttcat tttaaaaatg agagaaaaaa gagacagtgc   1860
ccctccccaa atatagagct atatatgtat attttatata tatagaattc attcgtgcac   1920
aattcattaa atgaacgtct caaaaattaa aaaaattata agatacgtat ttctttaggc   1980
ctttgtgttt ttaaattaaa accaacaaaa agaagtctcc ctctccactc cacccagcag   2040
caagggcagc cggaacgctt cgctccagct acccggcctc ccgcaagagg gttcccccat   2100
gagaccgtta gtctctcttt gcctggctga ctacctgcat acagtaggca ctcactgctg   2160
gagtgaggca ctgactcctc caaagattgc aggggggcgga ggagggaacc acgaaggcct   2220 gggaggggggc atctttggcc cccactaacc atctccctat ttctgcatcc tggtgaccgt   2280
cagcaagaga tgagtcgggg agaccctctc ctggagttct agcccctaat tctgggcttt   2340
ctatatgaga ggacatgcag atagggaaga aactaaaacc tttcaatgtc ttccttttt   2400 ctttaaaagt gtttcctcaa accatccccg tcccaaagag gccgccttgg gcaagtgcat   2460
gggagcccgg aagtggaact gaccaggtgg ggctccactg tcctgtgtgg gcgaagtgca   2520
aaaaaaaaaa aaaaaaaaa aaaaaagaaa gaaagaaaaa agaaaaacaa aagaaaaaag   2580
aaaaaccacc acaaaccaaa acaacaaaat gacacagaag agtgggcaaa aggggggatgt   2640 gtcctcttgg gtccccatag gccagagagg ctggtagcag tccagccccc tggccaaccc   2700
agctccctgt tggggctgac cctccagcct tgggcgggcc caccggcctg gctctcctcc   2760
aggacctcct ggctcagggg ctcgaggcca gtcttgtgct ggctccaggg cctgggccct   2820
gccttttaaa gggcttttcc ccataggcca aagcatcctg ggccccagtc cctgccgcat   2880
tcccccagtg aagcagctgc gcttctccaa aaccattttc acctcttcaa aaaggggcca   2940
tccccccaac tctgtccacc tcacactgaa gttggggact tgatcatcac ctcttcccag   3000
atcataggaa ggatgaggct cattttgacc ttgacccctt tgcagggtga gaacaaagag   3060
gggttgtggg cagctggggg ccccagtacc agcaaccttg accccccacc tggtactggg   3120
cagctgctct gacaccagca gcgctttctg aagagggctt gctacccaat acacccattt   3180
cacagaaggg caaactaaag gtcagagtgg gcacccagac agggatgggt cccaacttac   3240
cgtctcaaac cagagacacc agacctcacc ggtttcctat gatacttggg tggggagggg   3300
gcgcacttaa ggggagatga cggatgcccc aaccaatatt gaacgtagga ggagattggg   3360
ctttgggggt tatttcacat acaaaaataa agcaaaccag attgcaactt ctgcttggta   3420
attaggcaaa tggaaagcag caagggtgga cgaggggccc atggaggctg atctcccaag   3480
ggaggccgat ccgtgcaagt gtgtgggagg cggggggtact agagaggggga ggaaggaggc   3540 tccactcacc ctcggtccca tccactcggg ccccatggg cactgcccac ctcaaggcgg   3600
tgtgcctggt gcctcttcat gcaccaaggc tggcccgggc tgctccactt ggagctcagg   3660
ccagcagaag cagaccacct gtggcaaggg aaatgcattc cctctcccca gccacccca   3720 ggggcccagc ttcttgcctc ctgaagcctg catcccttt caggccaggg aggctcagag   3780
aggttgtggg ctttagggtg acccgtgggg agggaggtct cccccatagg gtggcggtgg   3840
tggggaccag atggcccaac aactgggaaa ggaacagaag ggggcaagaa accaaactgc   3900
ccactcacca gcccctgga gaaaatcacc agtgacaacc cccaccctcc caaacctcag   3960
cttgccggga cctgcagctt gggttagctc ccggggggccc gctgttgtcc ttcccttttga   4020 gcaagcacgg gtgtggagat ctgggtccag gccctctcca cagtgcctgc gatgccagggg   4080
```

-continued

```
gacctgccag ctgggcccag gcctccgccc catcctgaca ttgccacctc acctgtgcaa    4140
tcactgcgtt actatttttt cttaaatagc tctttctccc ccgccacccc cccataggaa    4200
tcccacaata tttttttcta tttctttttt ttttcctctt tttttgtttt tgtttttttg    4260
caaaactaat tctttcactt tcctgtcata aaatcacctc tgaaaacaca acttctttac    4320
aaaaaagtca cgaatgacac gaactctcag gaaaacacat ttctatggtc tctggaaaca    4380
cctgtaactg gcacccaggt ggtcactcac ctgggggagg gggtcagggg gaaatcacct    4440
ccaaggacag aggagaaata ccagccctta tttgggcgaa aagccaattg gcacttggac    4500
ggccacaaag ccaacacaca gggcagggta gggagggggcc gaggagtatc agccccccgcc   4560 ccaaccctgc gagggtcccc gttctacatc ccggggaggg gagggctagg gccacgctgt    4620
gggccctggc agggagattg ggaaggaagg cagcctccca ttcttaggac caaaggcgct    4680
agggttctga tcggcctcct gccaacgtgc ttctgaggga ggggcccatg gcagcacagc    4740
caggaagcca gctccagcca cgcctggaac acgccaccca cgcacaatgg agacccggga    4800
agtggcccag ggctggccag cggggccccg gtcccaattc tgggaccaac accctcattc    4860
tcctggagaa cacagaccct ctggtctccc ctttgcctgc ctgccctccc agggcctggc    4920
ctaaggctgg ggctgtggcc tctgccactg gcacgggtgc ctcagctccc aggcagcaga    4980
gggaaacaga agctgcccag gacacggggag cctcctttgc ttcaggcagg ctgggctgtg   5040
agaaagcctc cgtggtcaga agcaaaagag gggctgggac aagccgggag gccctcggga    5100
atggattctt cagcatcctc cccaaacacc cggaggaaga gggagcttgg aatggggtct    5160
ccctctctat ctcggtcccc accatgatgt gaagtgaagg tccgacaggt tgggctgacc    5220
accctgagga gggcagggggg gtggggggca cggtgccccc agcacacctg gccaggagg    5280 ggaggcctgg tgacttccac agcaaacctc cagacccaag cctggtcccc aggcctactg    5340
aggcgagagg cagtccaggc cttcaatgcc cctgttcaaa ggaactgtaa agggtgccac    5400
ccggcagcct ggggcctagc acccaatgca tgtatgaacc cacggacaaa cacagcgagt    5460
ggggcagacg cacaactgga agtttccacg gcaggttctc gtagcacctt tggtcaagaa    5520
ctgaaggggc ctttagatgc ggggaggctg tggccaggcg caccctctgc cagttcctcc    5580
caccgttgag ggggttagga aagagccagg gctggggcag ggcatagggg gtctacttag    5640
gcctcgtcca aaatcgagca gggaagaccc cgccctggcc caacttctga tgccctggct    5700
gatgtggagg gaggagccga gtcaggcctc atccttggcc tctgcctggg actttgccaa    5760
acaggcagga agccctcctc ctgcctaggc atctgcagga aggaaaggga ctgtgtccac    5820
cctcggtggg gggctcctaa gggccccaca gctgccaggt tagcaccgag aaatcagacg    5880
ccgcacagga gagcaggaag caagctagag agacaggtgg gatgtggaag gggcagagga    5940
accctagttt ctagggcttt ccagaaacca cccagtgggc taccatgcat gggcaggggg    6000
tgtgcccttc ccctgcccca ttccagggtg gccctaccc ccggctttct gggaccccaa     6060
ctacccagcc ccatccctgg gtcaacaccg agccatttga gacaagcaaa gcacaggagg   6120
agagggctgg gggcaagggt ggggtgggag caagagtatg acttcgggca ggagggcccc    6180
cccaagcccc cctccttggt ggagccccct cacttgctcg ccccaatgct gccaccgccc    6240
ccagcggcgc ctgctacccc agcagccacc ttctcgaaat cctcagggtt gcagaattcc    6300
ttgattgtga ccgtcaggag gttgctggtg acatcggtga cgaccacatt ggagcagggt    6360
gacatctcgg ggcgccagtc cccagcctcg ggctcggagg aggcaccggc gggctcaggg    6420
gccgtgggag gtgccgggcc ggcagcagct gtgacctcag gcggtgcccg cttgctggtg    6480
```

```
gctgccgact cgggagggag ggacaggtcg agcacctccg gctcgcgcca gctggggggcg    6540 gatgggctca cggtctcggg gaggagcttg gggggcgtgt cgtcggggtc agaggactgt    6600
ggtgtaggcg aggggcagcc ggaggagcca gagctgcggg cgtcgtaggg ggcggcgggg    6660
gcggccagaa gtagcccagg gcccgggggct gaggcctcag ccttgccggg ggacggggct    6720 accaggggggg cgggcggagg cttgtacagc gcaaaggcgc cgaacttcat gtggcggatc    6780
tgtgtacgca ggacgctctc gctgaacttc ttgctcttgc ctataacgcg gttccgcgag    6840
gggactttgg ggcgggccag cgccccggcc ccctgcccgg cgccccgcc gccagcgccc      6900 ttgtcgatca ccttcaggtt caggatgatg cggttccgct tgggctcccg cggcttcacc    6960
ttgcggttga tgatgcgcac cgtctccgag aagggcgaaa tgggcgggcg cagtccgggg    7020 ctgccccccct gcgggtccgg gcggggcagg ggacggcggg acatacggtg gcagcggcgg    7080
atgtccttct tgagccggtg cacggctgcg ctggagtgca gcttgggcga ggaggcactg    7140
gcgctcggct tgacagagaa atgcacatca ctgatgcgga gggcctcggc ctgggcccgc    7200
gcctgcgggc agagggaggg gtgggtggga cctcaggact gcccgctgac ctcccctgga    7260
tgtccctacg ccagccagcc ctaagtagag cctctcagcc agcgatcccg agatcattta    7320
agataatcac tggtcttcat gacctcgact tagaaaagga aacagaggtt cagagatgaa    7380
gcaatttgcc tctgactcca aggtcagagt caggacaccc ttgtccaggc ccaattccaa    7440
aactgtgttt tttctatcac ccaccacctc tgttagctcc acagagggcc ctgggccact    7500
ccatggctgc ccttgctgac acggaggagt gtcgacaatt gggacacagt gtcgggaggg    7560
cagccgtttg ctcagaagcc cctgctaaac ccctgctctg tggcagatcc agcccaagtg    7620
gggactcctc cacggactca ttcgtggtga cagaaaggag gaggtgggtc ctccctgctc    7680
ccccgcacca agtcctgctg agccaccatg tccccaatgc cccgtactct ctcgcctttg    7740
agcaggctga cctccggctc cagcctgtct cctcagctgg ccagcacctc agccaccata    7800
cttccctgga tgggtctcat ttacttgtct gcccagtgcc tggctcagag tgaactggta    7860
ccaatgcatc ccaaagcctg ggctggaacc caacccggtc agacgtgagt ttggtgggga    7920
caggcctaga agtgggcccg accactgcct attctctgtg ccaagatggt ctggggcagg    7980
atgatggtgc agaggtcgtg ggcagccagg aatactgccc caggctccca ggcctgtcct    8040
tccagctgtc cttccaggca tgaaatctct ttaaagccac agggctctca agagacccca    8100
ggttccggtc caacccaccc gttgtcagat gccactaaat ggagagaggc taagggactc    8160
ctaaggcgat gtaagctgtc tgcatggcca gtcctttctt tactaaggaa ggtactgagg    8220
caccaggcac cagttgcttg gggttacagc tgcacacgca cagactctcc cctggagagc    8280
tgccctatca cagggaggac ggtgggcagt gggaatatga agtgatttcg tgcagcgaaa    8340
gaaccacaga gcccagagaa gcacagaccc caggcttgga gaatgaaaca tcaaagcccg    8400
gccctgacac ctaagtagga aaaagtcctg gtccttactg agccctgact gcaccccaga    8460
cagttccaga ggctgcggtg gcctgctaag acagacagat ggtagaggca gagagtcctc    8520
tgggcaagat cccagtggtg tgagaagatg gcgaggagtc acaggactga aagcaagggc    8580
tggggacaga ggctgggggtg tgtgtggggt gccacaaggg gcgtgggttt tagagatcct    8640
actggggcag ggaggcttgt taggtgatgg ctgccctcaa tctaggtggg agatggttgg    8700
gaccgagaag aaggccatgt ccccacggtt ggtctgtgag gtccatgagg gtgggatctg    8760
ttgtgaggtc tctctacctc ccactcccca cagcattgga tgcttaacta gtacctggag    8820
```

-continued

```
gtagcccata tgcctctcag acaagactag attaccattt gatcacaact ctcaggagag    8880
atgtttgctg gcttatttgt tggctaagca aggatgtctt catttagaac gtggcgttca    8940
cccccatggg agaagggact gtgactccac gtggtcctcc cagcccaggc tggggcctcc    9000
tggggctgct tggttaacag tcccttccgc cactaggtgg cagcacatga agccgggcct    9060
gcccatgcca atgctgccag cccagctccc agggattggg cccctcagac cccttcccac    9120
acaaaggcag ggaaaagccc aggctttttt ggcgtggtaa gcagacattc tgcaggtgca    9180
tccccacact ttctgactct cagaaagtgt ttactccctc tgcaaactgc ctgagcttcc    9240
tgacttctga aattatgctt ccaagagtcc agtggtgacg gactgttcct gggggagggg    9300
cagagtgtgg gcaaatggca ggcccggaaa gaaaccctgg ctcagtgagt ctcctttcct    9360
tatctgctga accatcacag ggcctactac gggcactcct atgatgatca gagagtacat    9420
ggcacctgct cagcacagtg cctggcacgc agcaaataac tgaacagacc tacccatggg    9480
tggtggactt ataagcagtg atctttttcc aatgtatgct tggcatacat tgacatttct    9540
tactttatac tttctatata ttattatttt ttaaagggtt taccctttcct cttcctcccc    9600 acatggagaa ctctttgaaa gtgggacctg ggtctgcctg atgaattaaa aataactgta    9660
gccaacatgc ttattgcacc ctgaccaggt gacaggcata gctctgtggg cttggcaagc    9720
accgtagatg gtgtgaaggt ttaagcacct gaactctacc atggcctctc cccatgtctg    9780
tgggcaagtt actggacacc tctggccctg tttccccatg cgtgaaacag ggaggatgga    9840
agctatctca tgggctcctg tttgcttcag agtagttcct ggcagaaagc gctgagtgta    9900
atttgctgac tctgccatac tgcctctcag ggagccccag aacaatgtgt tcagcccaag    9960
ctaatctcca tagcccctca caaacatcca catcactctc aggctacctg tttcttaggg    10020
tccagataaa aaagtcctac tatctgtgtc tctatcccct gccacgccaa ctctgcagcc    10080
ttcatagttt cctgtgtgtg tctgccttcc ccctttaacc tgacatggac tactcaaggc    10140
acaagatgaa gaaaaggaga caggatgaag ccaggaagct ggacctcggg taagtcactt    10200
tcccttcctg ggccttgatt ttttatctgt gaaatgggga taatactcct tacttcttgg    10260
aactgttgaa agaattaaag gagataatcc atgtgggggc tcagccctgt attaggccca    10320
cagccagctc aggaaccaaa agaactatca agaaaaaaag gcgttctgtg tatcaatgct    10380
catggtcata ctcgcttcgc cgctagaggg tgccccagct gcactgagag gctgtcacac    10440
agcccaccag ccttccagct gctccgccca tccctcccca agagaagcat cagggttaag    10500
gttactccct ggatccccta ggatgtgcgt cgcttgaggg tggggggttat aaaaatatga    10560 aattctggaa accaacattt ctttcacttc tgcttctctt ctccgaaaaa gagtcctccc    10620
acaaagtcac cggctgtcgg gtgggagggg gccctgaggc atccgtagca ctacaggaag    10680 acaggggggcc cactgagtcc cacctgcagc cgtgcctgcc acctagggcc atcttgccct    10740
tcctttccca gactctgttt ttccttgtca aaataaaata aaaacccaaa tcctccaaga    10800
tggcttcctc tggaagttct tccctcccta gcagagacta atatgctatg ctctcactcc    10860
cacatcccca tccccagaa atggccggga gtggggggaa actgaggctc agagccctaa    10920
agttagtggc ccagcctggg tgataaattc aaagtaaaat gatttgaggt caaattcaag    10980
ttggatcccc aagaaaggag gggagccatg aagaacaaat cctgaaagac tgaacggggg    11040
aagctggggg cagggaggca ggtggtcccc caaatcctct ccttgtgccc tgccaggagg    11100
tgggacccca ctcactctcc ccctgggttc caactcccag cacagtcata acagctcaaa    11160
caaatgcccc cttcccatgg gcatccccca cctgcctcag ccacccccett tcctggagcc    11220
```

-continued

```
ctaaaggcat  ccccagcccc  tggtttcaac  agggaggatt  atcccagtc   ccaaaaccct   11280 cttgttgaag  ctgatgctgg  ctgaggcctg  ccatcagggg  cttctggggg  ggctcacaac   11340 cacccctgc   ccagctgggg  ccctctgaa   aaggccggcc  cgcttgggcg  gccgcgtatc   11400
tgtccctccc  ttccaggccc  cgtgctgtgc  cggggctggg  ggcccgagag  ggggatgctg   11460
ctggggctgg  gccaggttac  cttcaggagg  aaagttttgg  gtttgggtcc  cctcttcttg   11520
ggcccataca  gctcacgctc  cctctccctg  cggccgaaaa  acaccagagg  ttaaaaagag   11580
ccccttcccg  ggccccactc  cgcgctgccc  tccccggctc  tcccgcttcc  ccgcgcggcg   11640
ccccagccga  gcctcggcct  cgcagcccct  gccagcttcc  ccaacaactc  acttttgttc   11700
gaaggctgca  atgagccgcg  agtccaggat  gttctcctcg  ggctcccaag  tgctgtacct   11760
gccgagtcac  aaacgcacaa  aatcaggatg  aagaccagag  agggacaggc  acgcggcgag   11820
agcaagagcg  cgcacccca   ccccaggccc  cggtgcccgc  tgcctcccct  cccgcgacgc   11880
ccccggaccc  cgcgacactc  acttgatcgc  ccacccttc   catttcacca  ggtactcgat   11940
gcgtccctga  aaacagagg   ggagaaaaac  ggggtgggg   gtggggagga  tgcggggacg   12000
cgaggaggcg  gcggcgcggg  gctgggcgag  ggagccgggc  tagcgggacc  gcttcgcccc   12060
gagggccccc  ggccccggcc  ccggctgcgg  acagcggcgg  cccgccccgg  gcggcggctc   12120
acctttcgga  tccgccgttt  gatgatggat  tcggccgcga  agaccgctc   gcccactgca   12180 gacagctcca  tcttgctcag  cggcacccac  agcccataat  actccctgcg  cccgcggccg   12240
gtgcggcacc  gctcgcgcac  gcgccgcagc  gcccaggccc  cggcgggcgg  gagcgcggcg   12300
gggcgcgcgc  tcgcgttcca  gctgcgggcc  gtcacgtgat  cctcgcggct  ggcgcgcggt   12360
tgccaggacc  tcccctccc   ccggggcggt  tgctagggaa  agtcggcgct  cgcggggcgg   12420
gggcgcgcgc  tggctcttaa  aggggccgcg  cgggcggagg  gagcaattgc  cggccgaccc   12480
gatgggtgcc  cggcttgtgg  gcacgctgcg  gccttacgct  tatcacccc   cctcacatct   12540 tgccggcgcc  cgatcgctga  caccctctcc  ttgcctctta  atccccacgc  gagtctcgcc   12600
aggcccgggg  cggagaaggg  ctgtggagcc  cgagtctcgc  cgccaccgcg  catctcccgc   12660
agcagcctgc  aaacagttaa  atatgatgca  gcagaaatgc  agttgctgtt  gccttgccag   12720
gccttgcggg  aatttcttta  aaacatcgcc  ccccacccat  tatttatgta  ttcgtgggag   12780
ggtggttttg  taaccagttc  agaagagtta  aaacaaaaac  gccaccgcag  gaaggggggtg   12840 tgcggcgaat  ggggccgagg  aaggccggag  tgaccgtggg  catctgtctg  cggccggggt   12900
ctcgggcggc  acctgtcctc  gcccaggaga  ccggggagga  ttcggcgggg  ccggtgtggc   12960
agtgggggag  ggagagggac  cgcgggcagg  aacgggctcc  ccgcactccg  ccttgggccc   13020
acagcgggtc  atcatctggt  cattcggcag  aaaccgcctt  cgcggtcata  tctgtgtttt   13080
ccgattccca  gcaccctcc   cggccccccg  acctggccgc  gtccctctcc  ccgcccgcag   13140
ctgcgcgaag  cttccgccat  tgctctgggg  agcccagatc  ccagcttccc  acttgaggag   13200 gggcgggggga  tcgagctggg  gctgtccagg  aacggacaca  caaaaaatag  ccctgccgcg   13260
caaaacgctc  cactttttaa  atgttgaaat  tacttgaact  ttattttccca  ttatgttagt   13320 agtcttgttc  tttgtaaaac  aattttaaaa  atacagataa  aacaactgtc  cataacccc    13380 ataaaaccat  tgttaacatc  ttcaccaatc  ttccagcctc  tgctctatgc  gtacataaac   13440
tcacgtacac  ctatgtatgt  atgtatatac  atacacatac  acattgtctg  tagatttaat   13500
tttttaacaa  aatgggatca  cgctattcac  actgttctgg  aatctgcttt  tctcccttaa   13560
```

-continued

```
tgctataaag tggacatctt tcagtgtcat taaatacaga tttcaccatc cttccagtga    13620
ccaccttggg gctgagatgg ggtgggagg aatggggatt gtgaagagtc agggttgtgt      13680
cttgcgaaca tcaatggctc attaggaaag atttttgcgt ttctgtgcta caatgccaat    13740
tcttgggttt caaatccacc atagcaaaat gttagtcttt ttctcccagc agatttgtcc    13800
aattattacc ttgagagaaa tccctctcct cacttaaaat cagtatgttc cagggaaaca    13860
gctatttgct ggccagccca aggtgagctg ctgtggtaaa aatagaaatg tcctcctggg    13920
agatgtgggt ggtggtgggt gagcaggtga gaggagtggg tatgacagtg tgtgtgtgtt    13980
caggctgacg gagacaggcg ggggatgaag caggtgagtc cacttgttga ttcattcagc    14040
agtgtttgtg agcccttgtg aagcaccagg ctttgtgtga aaccatcagg aaacaaaggt    14100
gccccaggct gaggagctgt cagtggagtg agaacggcac ctgtcacaca gtgtgactaa    14160
tgctagaata aaggtgtagg agtttcgtgt tgctgctctc acaaattaac acaagctcag    14220
tggcttaaaa tgactcacat ttgttatctg atgactctgg aggcgggaag tcccaaatca    14280
gtgttactgg gcccaagtga aggtatcctc agggctggtc cctttttgga gggtcaagga    14340
gagtatctgt tccgtgcctc atccagcttc caaatgttgc tggcatttct tggctcatgg    14400
cttcatcact caaatctctg tttccacgat ccctttgctc acttcctgct tctttctttc    14460
ttttgttttt gtttttgaga tggagtcttg ctcagtcacc caggtgggag tgcagtggca    14520
caatctcggc tcactgcaac ctctgcctcc cggtttcaaa caattctccc agtctcagcc    14580
tcccaagtag ctgggattac aggcatgcgt caccacaccc ggctaatttt tgtatttagt    14640
agagatgggg gtttcaccat gttagccagg ctggtctcga actcctgacc tcaagtaatc    14700
cacccgcctc agcctcccaa agtactggga ttacaggcgt gagccaccgc acctggcttc    14760
tgcctctttc ttttaacaac acttgtgatt acattgggtc tgcccaaata attgagaatg    14820
atctttccgt ctcaacctca acttaatcag atttgcaaag accctcttac catagggtaa    14880
catggatggt aagtaaggta tcctatccac aggttctggg ggctaggggc taggacacgg    14940
acatctttcg gggaggcatt ataagcctgc cacaagagtc tgtacaggat gtcttgggag    15000
t                                                                    15001
```

<210> SEQ ID NO 2
<211> LENGTH: 497
<212> TYPE: DNA
<213> ORGANISM: Homo sapiens

<400> SEQUENCE: 2

```
ccagattgca acttctgctt ggtaattagg caaatggaaa gcagcaaggg tggacgaggg      60
gcccatggag gctgatctcc caagggaggc cgatccgtgc aagtgtgtgg gaggcggggg     120
tactagagag gggaggaagg aggctccact caccctcggt cccatccact cgggccccca     180
tgggcactgc ccacctcaag gcggtgtgcc tggtgcctct tcatgcacca aggctggccc     240
gggctgctcc acttggagct caggccagca gaagcagacc acctgtggca agggaaatgc     300
attccctctc cccagccacc cccagggggcc cagcttcttg cctcctgaag cctgcatccc     360
ctttcaggcc agggaggctc agagaggttg tgggctttag ggtgacccgt ggggagggag     420
gtctccccca tagggtggcg gtggtgggga ccagatggcc caacaactgg gaaaggaaca     480
gaagggggca agaaacc                                                     497
```

<210> SEQ ID NO 3
<211> LENGTH: 25

-continued

```
<212> TYPE: DNA
<213> ORGANISM: Homo sapiens

<400> SEQUENCE: 3
ttagattgta atttttgttt ggtaa                                          25

<210> SEQ ID NO 4
<211> LENGTH: 22
<212> TYPE: DNA
<213> ORGANISM: Homo sapiens

<400> SEQUENCE: 4
aatttcttac ccccttctat tc                                             22

<210> SEQ ID NO 5
<211> LENGTH: 20
<212> TYPE: DNA
<213> ORGANISM: Homo sapiens

<400> SEQUENCE: 5
ggaaagtagt aagggtggat                                                20

<210> SEQ ID NO 6
<211> LENGTH: 18
<212> TYPE: DNA
<213> ORGANISM: Homo sapiens

<400> SEQUENCE: 6
ccctctctaa taccccca                                                  18

<210> SEQ ID NO 7
<211> LENGTH: 28
<212> TYPE: DNA
<213> ORGANISM: Homo sapiens

<400> SEQUENCE: 7
ttgatttgtg taagtgtgtg ggaggtgg                                       28

<210> SEQ ID NO 8
<211> LENGTH: 20
<212> TYPE: DNA
<213> ORGANISM: Homo sapiens

<400> SEQUENCE: 8
ggaaagtagt aagggtggac                                                20

<210> SEQ ID NO 9
<211> LENGTH: 18
<212> TYPE: DNA
<213> ORGANISM: Homo sapiens

<400> SEQUENCE: 9
ccctctctaa taccccccg                                                 18

<210> SEQ ID NO 10
<211> LENGTH: 28
<212> TYPE: DNA
<213> ORGANISM: Homo sapiens

<400> SEQUENCE: 10
tcgattcgtg taagtgtgtg ggaggcgg                                       28
```